(12) United States Patent
Van Der Hulst et al.

(10) Patent No.: US 11,266,806 B2
(45) Date of Patent: Mar. 8, 2022

(54) SLEEP TRAINER WITH HEART RATE MEASUREMENT BAND

(71) Applicant: KONINKLIJKE PHILIPS N.V., Eindhoven (NL)

(72) Inventors: Robert Franciscus Van Der Hulst, Leiden (NL); Guus De Hoog, Amsterdam (NL); Thijs Van Oorschot, Leiderdorp (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 400 days.

(21) Appl. No.: 16/328,320

(22) PCT Filed: Sep. 1, 2017

(86) PCT No.: PCT/NL2017/050578
§ 371 (c)(1),
(2) Date: Feb. 26, 2019

(87) PCT Pub. No.: WO2018/044170
PCT Pub. Date: Mar. 8, 2018

(65) Prior Publication Data
US 2021/0283364 A1    Sep. 16, 2021

(30) Foreign Application Priority Data
Sep. 2, 2016 (NL) ...................................... 2017406

(51) Int. Cl.
*A61M 21/02* (2006.01)
*A61M 21/00* (2006.01)

(52) U.S. Cl.
CPC ..... *A61M 21/02* (2013.01); *A61M 2021/0022* (2013.01); *A61M 2209/088* (2013.01);
(Continued)

(58) Field of Classification Search
CPC .............. A61M 21/02; A61M 2230/06; A61M 2209/088; A61M 2230/65; A61M 2021/0022; A61M 2230/40
(Continued)

(56) References Cited

U.S. PATENT DOCUMENTS 4,129,125 A     12/1978  Lester et al.
4,895,162 A *    1/1990  Dolliver ............... A61B 5/1135
                                                      600/534
(Continued)

FOREIGN PATENT DOCUMENTS

DE    102012107855 A1    5/2014
EP         1494580 A1    1/2005
WO      1998041279 A1    9/1998

OTHER PUBLICATIONS

C. C. Oliveira, J. Machado da Silva, I. G. Trindade and F. Martins, "Characterization of the electrode-skin impedance of textile electrodes," Design of Circuits and Integrated Systems, 2014, pp. 1-6, doi: 10.1109/DCIS.2014.7035526. (Year: 2014).*

*Primary Examiner* — Navin Natnithithadha
*Assistant Examiner* — Sunita Reddy (57) ABSTRACT

Sleep trainer (1) comprising a band (2) with two electrodes (21), (22) for carrying out an impedance measurement and a monitor (3) for receiving a measurement signal. The band has a band pocket (23). An electrical connection is obtained by inserting the monitor (3) into the band pocket (23). Band contact points ((210),220) are provided inside the band pocket (23). Monitor contact points (31), (32) are provided at an external surface of the monitor housing (30). The monitor contact points are flat and hardly protrude above the monitor housing. The band pocket (23) prevents a lateral movement of the monitor and a band pocket wall (231) exerts a pressing force to keep the monitor contact points (31), (32) in an abutting engagement with the band contact
(Continued)

points (210), (220). Advantageously, the sleep trainer provides a high level of wearing comfort which contributes to a sleep disorder treatment compliance.

20 Claims, 3 Drawing Sheets

(52) U.S. Cl.
CPC ..... *A61M 2230/06* (2013.01); *A61M 2230/40* (2013.01); *A61M 2230/65* (2013.01)
(58) Field of Classification Search
USPC ..................................................... 600/26–28
See application file for complete search history.

(56) References Cited

U.S. PATENT DOCUMENTS

| | | | |
|---|---|---|---|
| 5,016,636 A * | 5/1991 | Kulakowski | A61B 5/0205 600/390 |
| 5,913,834 A | 6/1999 | Francais | |
| 6,047,203 A * | 4/2000 | Sackner | A61N 1/0452 600/388 |
| 8,142,373 B1 | 3/2012 | Riles | |
| 2004/0073127 A1 | 4/2004 | Istvan et al. | |
| 2005/0119701 A1* | 6/2005 | Lauter | A61B 5/282 607/2 |
| 2006/0276718 A1* | 12/2006 | Madaus | A61B 5/1135 600/538 |
| 2008/0119896 A1* | 5/2008 | Wong | A61N 1/3601 607/2 |
| 2008/0264426 A1* | 10/2008 | Walker | A61B 5/486 128/848 |
| 2009/0076364 A1* | 3/2009 | Libbus | A61B 5/282 600/391 |
| 2010/0056882 A1* | 3/2010 | Moore | A61B 5/14552 600/301 |
| 2011/0087115 A1 | 4/2011 | Sackner et al. | |
| 2012/0143020 A1 | 6/2012 | Bordoley et al. | |
| 2012/0146797 A1 | 6/2012 | Oskin et al. | |
| 2015/0343196 A1* | 12/2015 | Vasapollo | A61N 1/36025 607/45 |
| 2017/0007129 A1* | 1/2017 | Kaib | G06F 19/00 |
| 2018/0184735 A1* | 7/2018 | Longinotti-Buitoni | A61B 5/6843 |

\* cited by examiner

SLEEP TRAINER WITH HEART RATE MEASUREMENT BAND

Cross-Reference to Prior Applications

This application is the U.S. National Phase application under 35 U.S.C. § 371 of International Application Serial No. PCT/NL2017/050578, filed on 1 Sep. 2017, which claims the benefit of Dutch Application Serial No. 2017406, filed on 2 Sep. 2016. These applications are hereby incorporated by reference herein.

The invention relates to a sleep trainer. The sleep trainer is an apparatus which is arranged to provide an alert during a person's sleep in response to an impedance measurement. In particular, the invention relates to a sleep position trainer. The sleep position trainer is arranged to provide an alert during a person's sleep to stimulate a change in a sleep position. Further, the invention relates to an impedance measurement band for a sleep trainer and a monitor for a sleep trainer for receiving an impedance measurement signal.

WO98/41279 discloses a feedback system which can be used for the treatment of an obstructive sleep apnea syndrome. The feedback system includes a garment with electrocardiogram electrodes and sensors which are attached to the garment. The garment is in the form of a shirt and fits over a torso of a patient to be monitored. The sensors are in direct skin contact. The sensors generate signals in response to the physiological signs of the patient. The feedback system comprises for instance a body position sensor and a heart rate sensor. The signals are transmitted to a recording/alarm device where they are monitored for adverse conditions and logged. When an adverse condition or other pre-programmed condition occurs, a message is communicated to the patient by either an audio message or a display. Further, the feedback system may comprise a microcontroller unit that is attached to or carried on the garment. The sensors are connected to the microcontroller unit. The microcontroller unit may include or activate a signalling device to effect a vibration which will be felt by the patient being monitored.

A disadvantage of this known feedback system is that this system lacks comfort during use. The bulky components connected to the garment are obstructive and are disturbing a person's sleep. The bulky components may prevent a user to sleep in a preferred posture.

EP1494580 discloses a wearable monitoring system including a fabric-based elastic belt for housing electrodes. The wearable monitoring system aims to be user-friendly in wearing the system during sleep. In particular, it is aimed to increase comfort when the elastic belt is being worn by a patient during a long period of time. A storage and analyses device to be attached to the belt is mentioned, but the disclosure is silent about a proper structure of a connection of such a storage and analyses device.

U.S. Pat. No. 4,129,125 discloses a patient monitoring system in which a device is mounted to an elastic band to be worn around a patient's waist and in contact with his skin surface. The device has a circular housing which is connected to the belt by means of spring-loaded pins.

A drawback of this mounting of the device is that it provides hard protrusions and makes the patient monitoring system bulky. When lying on the monitoring system, the monitoring system will press on to a patient's body. A patient who is wearing the monitoring system will be disturbed during his sleep and experience the monitoring system as being obstructive. Discomfort of the monitoring system may make a treatment of a sleep disorder ineffective. Such a discomfort will lead over time to a non-compliance to a treatment protocol. Finally, this will lead to a non-acceptance of the system in a treatment of sleep related problems. A monitoring system having a high degree of comfort is for that reason required to obtain treatment compliance.

DE 102012107855 discloses another mounting of a monitoring device to a heart rate belt. The mounting includes a snap fastener set including a male press stud which is connected to the belt and a corresponding female side part connected to the device. The monitoring device can be releasably connected to the belt by pressing the device onto two press studs. The press studs form a mechanical connection of the monitoring device to the belt and at the same time provide an electrical connection of an electrode of the belt to the monitoring device.

A drawback of this known mounting of the monitoring device is that also this mounting provides too much discomfort to a patient. This discomfort may lead to a non-compliance in a sleep disorder treatment which is unacceptable.

The general object of the present invention is to at least partially eliminate the above mentioned drawbacks and/or to provide a useable alternative. More specifically, it is an object of the invention to provide a sleep trainer including an elastic band and a monitoring device, a so-called monitor, which in an assembly provides an increased wearing comfort to a patient to obtain a high level of compliance in a sleep related treatment.

According to the invention, this object is achieved by a sleep trainer according to claim 1.

According to the invention a sleep trainer comprising a band including at least two electrodes for carrying out an impedance measurement, preferably a thoracic impedance measurement and a monitor for receiving a measurement signal from the electrodes is provided. The impedance measurement may be carried out for determining a heart rate and/or a respiration measurement. The monitor is releasable connected to the band to allow a user to manually remove the monitor from the band. The band includes a band body comprising a first electrode and a second electrode, in which each electrode has an electrode distal end comprising a sensor pad exposing at an external surface at an inner side of the band. The sensor pad is arranged for a skin contact. Each electrode has an electrode proximal end which is exposed at an externally accessible surface of the band to form a band contact point. The band has a band pocket for receiving the monitor in which each band contact point is positioned inside the band pocket. The band pocket has a band pocket opening for inserting the monitor into the band pocket. The band pocket opening allows an access from the outside to the band contact point.

The monitor includes a monitor housing for housing electrical components. The monitor is provided with a first and second monitor contact point which are positioned at an external surface of the monitor for electrically connecting the monitor to respectively the first and second band contact point of the first and second electrode. The band and monitor contact points are arranged to obtain the electronic connection by an abutting engagement of the contact points. The band pocket is dimensioned in correspondence with the monitor housing to mate the monitor contact points with the band contact points. The band pocket accurately positions the monitor with respect to the band. Particularly, the size of the band pocket is in correspondence with an outer contour of the monitor housing to obtain a close fit. The monitor closely fits inside the band pocket. The band pocket determines the position of the monitor with respect to the band contact points. The band pocket prevents a lateral movement of the monitor with respect to the band. The band pocket has a band pocket wall which is stretchable to press the monitor contact points onto the band contact points.

After inserting the monitor into the band pocket, the band pocket prevents a shifting of the monitor and the monitor is maintained in position with respect to the band. A presence of a tension generated by the elastic pocket wall keeps the contact points of the monitor and the band in contact. Advantageously, the abutting engagement of the monitor contact points onto the band contact points allows a flat-structure of an assembly of the monitor onto the band. The flat-structure contributes to a high comfort level of the sleep trainer. The flat-structure may eliminate a feeling of an obstacle to a patient who is wearing the sleep trainer when the patient lies on the monitor. A sleep disorder treatment generally requires a long wearing time of several hours on a daily basis. The sleep trainer according to the invention provides a high level of wearing comfort which is required in a sleep disorder treatment to prevent the sleep trainer to be a negative factor in a patient's sleep. Advantageously, the sleep trainer according to the invention strongly reduces a risk of a non-compliance to a sleep disorder treatment. Herewith, the sleep disorder treatment is suitable to be used in a sleep disorder treatment.

The sleep trainer according to the invention may provide several additional advantages.

The monitor is releasable from the band by taking the monitor out of the band pocket. A user may manually remove the monitor from the band pocket. The monitor may e.g. be released from the band for cleaning the band without electronic components or e.g. for retrieving stored data from the monitor.

A further advantage of the band pocket may be that even in a dark environment the presence of the band pocket may enable a user to easily insert or remove the monitor of the sleep trainer.

In an embodiment of the sleep trainer according to the invention the first and second monitor contact points are flat. The monitor contact points comprise a flat top surface. In principle, the flat monitor contact points do allow a lateral movement in an abutting engagement with the band contact points. However, according to the invention, the lateral movement is constrained by the close fit of the band pocket around the monitor. In particular, the first and second monitor contact points are cylindrical and coin-shaped. Preferably, the flat monitor contact points protrude at most 1.0 mm, in particular at most 0.5 mm, more in particular at most 0.3 mm, above an external surface of the monitor housing. The flat contact points contribute to a flat-design of the monitor. The monitor may have a minimal height which contributes to a wearing comfort when wearing the sleep trainer during a sleep. The user may lie on the monitor during its sleep without experiencing the monitor as an obstructive uncomfortable item.

In an embodiment of the sleep trainer according to the invention, the first and second monitor contact points are spaced at a distance from each other. Preferably, the first and second monitor contact points are spaced at a pitch of at least 5 mm, in particular at least 10 mm from each other. Advantageously, such a distance in between the band and the monitor contact points prevents an electronic interference of measurement signals conducted by the first and second electrode. Additionally, a mis-alignment of the contact points may also be prevented.

In an embodiment of the sleep trainer according to the invention, the first and second electrode are formed by an electrical conductive fabric. The conductive fabric is connected to a support material which forms the band body. Preferably, the conductive fabric is connected to an inner side of the band body. The conductive fabric may be of a non-irritating material, in particular anti-bacterial material and may form an external surface section of the band which may come in skin contact. Preferably, the sensor pad is formed by the exposing surface section of the conductive fabric. Herewith, the conductive fabric advantageously incorporates a sensor pad. No separate components forming a sensor pad are necessary.

Advantageously, the conductive fabric contributes to a flexibility of the band and contributes to a wearing comfort of the sleep trainer. The sleep trainer is soft and comfortable in use. Preferably, the conductive fabric is laminated to the layer of support material. In particular, the conductive fabric is oblong. The electrode may be a strip of conductive fabric. The oblong conductive fabric may have a length of at least 5 cm, in particular at least 10 cm. The elongated conductive fabric has a distal end which functions as a sensor pad and a proximal end which is positioned inside the band pocket which functions as a band contact point.

In an alternative embodiment of the sleep trainer according to the invention, an electrode of the band may include an electric wire. The electric wire may be woven in a stretchable fabric attached to the band body. The proximal end of the electric wire may be connected to a separate component which form the band contact point. The distal end of the electric wire may be connected to a sensor pad formed by a separate component.

In an embodiment of the sleep trainer according to the invention, the sensor pad as a separate component may be permanently attached to the band of the sleep trainer. In an alternative embodiment, the sensor pad may be a separate item connectable with the electrode of the band. The sensor pad may be a separate sticker sensor pad as e.g. known from an ECG (electrocardiography) measurement. In an initial step, the sticker sensor pad may be adhered to a human body, were after the band of the sleep trainer is connected to these sticker sensor pads. Advantageously, the sticker sensor pads allow an accurate positioning of the sensor pads which may be desired in a sleep treatment.

A sleep trainer may for example provide an alert in an event that during a sleep a predetermined heart rate is reached, e.g. to alert for a minimum or maximum heart or respiration rate. Preferably, the sleep trainer comprises a vibrator to provide a tactile stimulus in response to a detection of a predetermined event. Advantageously, a tactile stimulus may alert a patient without disturbing a sleeping environment of the patient, e.g. a bed partner may sleep undisturbed without noticing the vibration.

In an embodiment of the sleep trainer according to the invention the band pocket is positioned at the band inner side. The band pocket wall is positioned at the band inner side.

The band pocket wall is positioned at a backside of the band body. The pocket for receiving the monitor is provided in between the band body and the band pocket wall at the backside of the band body. The band pocket opening is preferably positioned at the front side of the band body to allow a user to insert the monitor from a front side of the band while wearing the band. The band pocket opening may be formed by a slotted through hole through the band body to allow a monitor to pass to receive the monitor in the band pocket. Preferably, the band pocket wall is made of a stretchable fabric. Preferably, the fabric has a thickness of at most 0.5 mm. In use of the sleep trainer, a received monitor inside the band pocket is positioned in between the band body and a user's body. Preferably, the vibrator for providing a tactile stimulus is housed in the monitor housing. Advantageously, such a positioning of the monitor at an inner side of the band contributes to an improved transfer of tactile stimuli to the user's body. Only a piece of thin fabric forming the band pocket wall needs to be positioned in between the monitor and a skin of the user's body for pressing the contact points. The thin fabric contributes to an optimal transfer of a tactile stimuli.

In an embodiment of the sleep trainer according to the invention, the band contact points are positioned on the band pocket wall. Preferably, the each electrode comprises a strip of conductive fabric having a proximal end which is attached to the band pocket wall. Preferably, the band pocket wall including the conductive fabric is more stretchable than the opposite positioned band body which contributes to a reliable pressing of the monitor against the band body.

In an embodiment of the sleep trainer according to the invention, the sleep trainer is a sleep position trainer. The sleep position trainer is provided with a position sensor for detecting a body posture of a person wearing the sleep position trainer. Advantageously, the sleep position trainer is suitable to be used in a sleep treatment for reducing an apnoea risk. The position sensor may e.g. detect an upright position or a lying position. Preferably, the position sensor is arranged to detect a particular lying position, e.g. a supine lying position or side lying position. The sleep position trainer is programmed to provide a predetermined alert in response to a detection of a predetermined position. The sleep position trainer alerts and stimulates the patient to change position during a sleep when sleeping in a predetermined wrong position, e.g. a supine posture. The sleep position trainer may alert and stimulate the patient to turn to another position. The sleep position trainer trains a person to sleep in a correct position. Herewith, the sleep position trainer is suitable in a sleep disorder treatment in which a sleep position plays a role.

In an embodiment of the sleep trainer according to the invention, the monitor is positioned at the band, such that in wearing the sleep trainer, the monitor is positioned at a central position of the human's torso. Herewith, the monitor is positioned at a position of the human's torso which provides hardly no obstruction during sleep which contributes to a comfortable use. In particular, the monitor may be positioned at a region of a chest band at a distance of at least 20 cm and at most 50 cm from a first end of the chest band, such that the monitor is centrally positioned with respect to a human's body and a closure of the chest band is positioned within reach when putting the chest band on.

In an embodiment of the sleep trainer according to the invention, the monitor is positioned in between the first and second electrode. Instead of an arrangement of electrodes at one side of the monitor, electrodes are arranged at both sides of the monitor. The first electrode forms a left electrode which is positioned at a left side of the monitor and the second electrode forms a right electrode which is positioned at a right side of the monitor.

In an embodiment of the sleep trainer according to the invention, the band is incorporated into a garment. The band of the sleep trainer may be incorporated in a T-shirt which fits tight around a human's torso or neck. The band pocket for receiving the monitor may be incorporated in the garment.

In an embodiment of the sleep trainer according to the invention, the band is a strap. Preferably, the strap is a chest strap. The chest strap is arranged for circumventing a torso of a human body. The first and second electrodes are arranged to carry out a thoracic electrical bio-impedance (TEB) technology measurement. Thoracic means that the electrode sensor pads are located at a human's chest to carry out an impedance measurement. Impedance measurements can be used non-invasive to determine all kind of body parameters, like continuous measurement of global blood flow (Cardiac Index, CI—the global blood flow per minute, and Stroke Index, SI—the global blood flow per beat), respiration and a host of cardio dynamic parameters. At its free ends, the strap may have closure members, like Velcro components to provide a closure.

In an alternative embodiment of the sleep trainer according to the invention, the band is a strap which is arranged to be worn around a neck of a person. This strap, also called a neck strap is arranged for circumventing a neck of a human body. At its free ends, the neck strap may have closure members, like Velcro components to provide a closure.

In an alternative embodiment, the strap is a separate component which is arranged to fit into a garment like a T-shirt or a pyjamas vest. The strap may be received in a dedicated sleeve of the garment.

In an embodiment of the sleep trainer according to the invention, the monitor housing is a moulded item, in particular an injection moulded item. The monitor housing is made of a plastic material. The monitor housing houses electronic components for receiving a measurement signal from an electrode. The electronic components are separate components to be built into the monitor housing. The moulded monitor housing provides a hard casing to protect the electronic components. The monitor housing has a housing top surface. The monitor contact points are positioned at the housing top surface. In use, the monitor is enclosed in the band pocket which may contribute to a softening of the hard case. The band pocket wall may include a soft fabric at an outer side, in particular a knitted fabric material to contribute to a wearing comfort of the sleep trainer.

In an embodiment of the sleep trainer according to the invention, the monitor is a layered item in which the monitor housing is a baseplate for supporting electronic components. The monitor may be manufactured by a layering process. The monitor may be manufactured by composing several layers on each other. As in manufacturing a printed circuit board, electronic components, like a chip or battery, may be mounted on the base plate by a soldering process. The monitor has a layered structure of a baseplate forming a ground layer and a layer of electronic components on the baseplate. In particular, the electronic components are additionally covered by a protective layer. At at-least one side of the monitor, the monitor is provided with monitor contact points.

The monitor contact points may be manufactured by a step in the layering process, e.g. by a vapor deposition step. Advantageously, the monitor structured as a layered item may have a minimum height of at most 3 mm, in particular at most 2 mm, which improves wearing comfort.

Further, the invention relates to a band for a sleep trainer according to the invention. The band includes at least two electrodes for carrying out an impedance measurement. The band includes a band body comprising a first electrode and a second electrode. Each electrode has an electrode distal end comprising a sensor pad which is exposed at an external surface at an inner side of the band. The sensor pad is arranged for a skin contact. Each electrode has an electrode proximal end which is exposed at an external surface of the band to form a band contact point. The band has a band pocket for receiving a monitor which is arranged for receiving a measurement signal from the electrodes of the band. The band contact points are positioned inside the band pocket. The band pocket has an elastic band pocket wall for pressing monitor contact points of a received monitor onto the band contact points.

Further, the invention relates to a monitor for a sleep trainer according to the invention. The monitor is releasable connectable to a impedance measurement band to allow a user to manually remove the monitor from the band. The band includes a band body comprising a first electrode and a second electrode, in which each electrode has an electrode distal end comprising a sensor pad which is exposing at an external surface at an inner side of the band. The sensor pad is arranged for a skin contact. Each electrode has an electrode proximal end which is exposed at an external surface of the band to form a band contact point. The band has a band pocket for receiving the monitor in which each band contact point is positioned inside the band pocket. The monitor includes a monitor housing for housing electrical components. The monitor housing is provided with a first and second monitor contact point which are positioned at an external surface of the monitor housing for electrically connecting the monitor to respectively the first and second band contact point of the first and second electrode. The band and monitor contact points are arranged to obtain the electrical connection by an abutting engagement of the contact points. The band pocket is dimensioned in correspondence with the monitor housing to mate the monitor contact points with the band contact points. The band pocket has a band pocket wall which is elastic to press the monitor contact points onto the band contact points.

In an embodiment of the monitor according to the invention, the first and second monitor contact points are flat. In particular, the monitor contact points protrude at most 0.5 mm, in particular at most 0.3 mm, above an external surface of the monitor housing. In particular, the first and second monitor contact points are spaced at a distance, in particular at a pitch of at least 5 mm, from each other. In an embodiment, the monitor housing is a moulded item, in particular an injection moulded item.

In a particular embodiment of the monitor according to the invention, the monitor has monitor contact points at both sides of the monitor housing. Advantageously, a double arrangement of monitor contact points makes a particular orientation of the monitor for introducing the monitor into the band pocket redundant.

The invention will be explained in more detail with reference to the appended drawings. The drawings show a practical embodiment according to the invention, which may not be interpreted as limiting the scope of the invention. Specific features may also be considered apart from the shown embodiment and may be taken into account in a broader context as a delimiting feature, not only for the shown embodiment but as a common feature for all embodiments falling within the scope of the appended claims, in which:

Identical reference signs are used in the drawings to indicate identical or functionally similar components.

Figure 1:
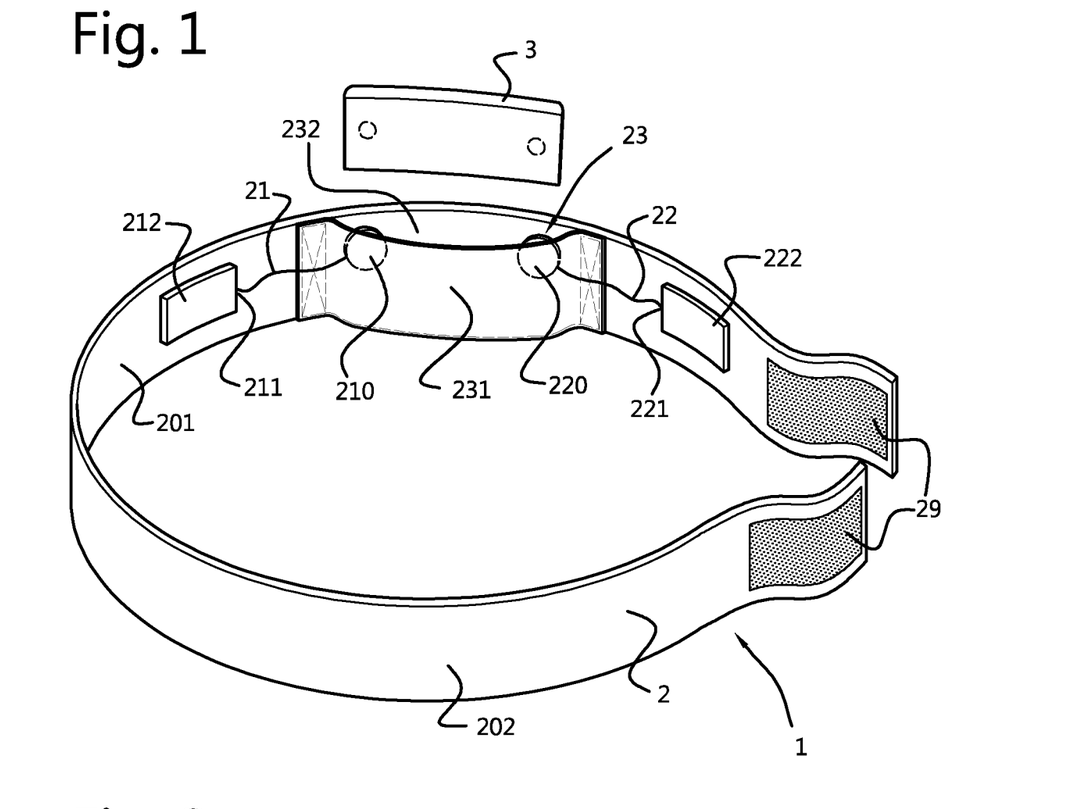
FIG. 1 shows a perspective exploded view of the sleep trainer according to the invention including a band and a monitor for processing thoracic impedance measurement signals.

FIG. 1 shows in a perspective view a sleep trainer 1. The sleep trainer 1 is arranged for improving a sleep quality of a person.

The sleep trainer 1 comprises a band 2, also called a waist band, chest band or chest strap, which is arranged to be worn around a chest of a person. The band includes two electrodes 21, 22 at a band inner side 201 for carrying out a thoracic impedance measurement. The thoracic impedance measurement can be used to determine a heart rate or a respiration measurement. The electrodes 21, 22 are attached to a band body 20. Each electrode 21, 22 has an electrode distal end connected to a sensor pad 212, 222. The sensor pads 212, 222 are positioned at an external surface at the inner side of the band to obtain skin contact when wearing the sleep trainer 1. Each electrode 21, 22 has an electrode proximal end which is exposed at an external surface of the band to form a band contact point 210, 220.

Preferably, the band contact points 210, 220 are positioned at the inner side of the band 201.

Further, the sleep trainer 1 comprises a monitor 3 for receiving and processing a measurement signal from the electrodes. The monitor 3 may include a memory for storing received measurement data. The monitor 3 may include a processor for processing measurement data to provide output data.

Figure 5:
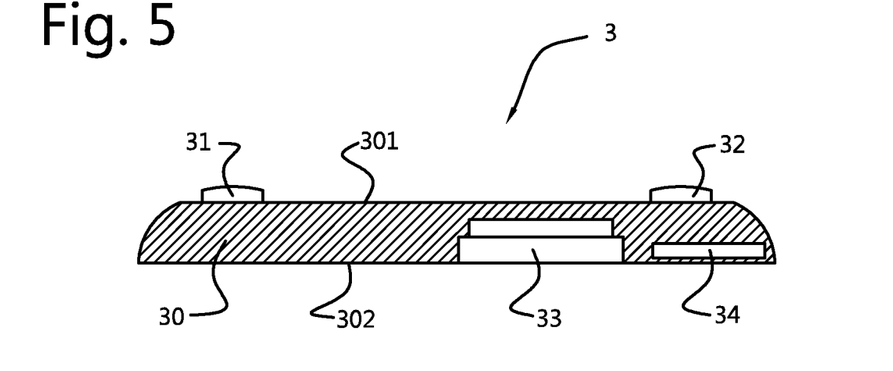
FIG. 5 shows a cross sectional view of the monitor including a vibrator and a position sensor.

As further illustrated in FIG. 5, the monitor 3 includes a monitor housing 30 for housing electronic components, like a memory, processor chip, battery etc. The monitor housing 30 is made of a plastic material by injection moulding. The monitor housing 30 has a flat-structure including a housing top surface 301 and a housing bottom surface 302. The monitor housing 30 has a limited height of at most 5 mm, in particular at most 3 mm. The limited height advantageously contributes to a wearing comfort.

Figure 2:
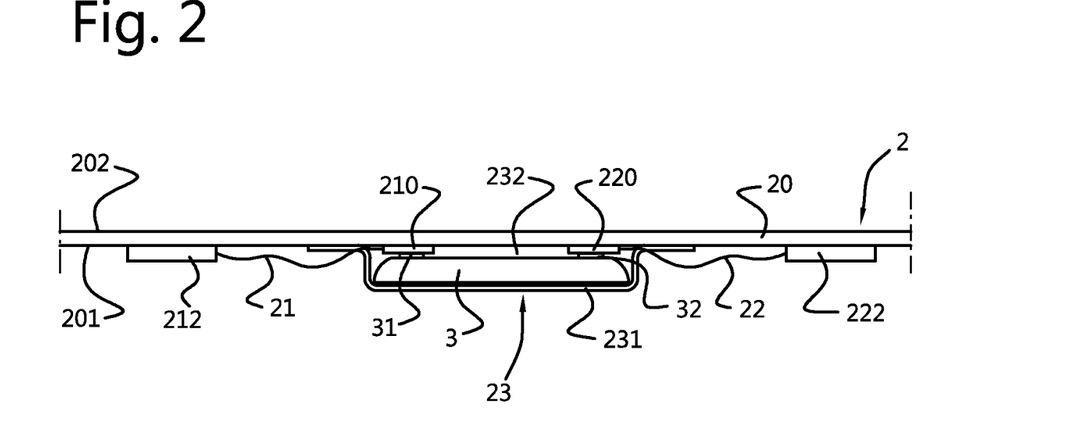
FIG. 2 shows a cross sectional view of the band as shown in FIG. 1 including a band pocket for receiving the monitor, wherein monitor contact points are directed to a band body of the band.
Figure 3:
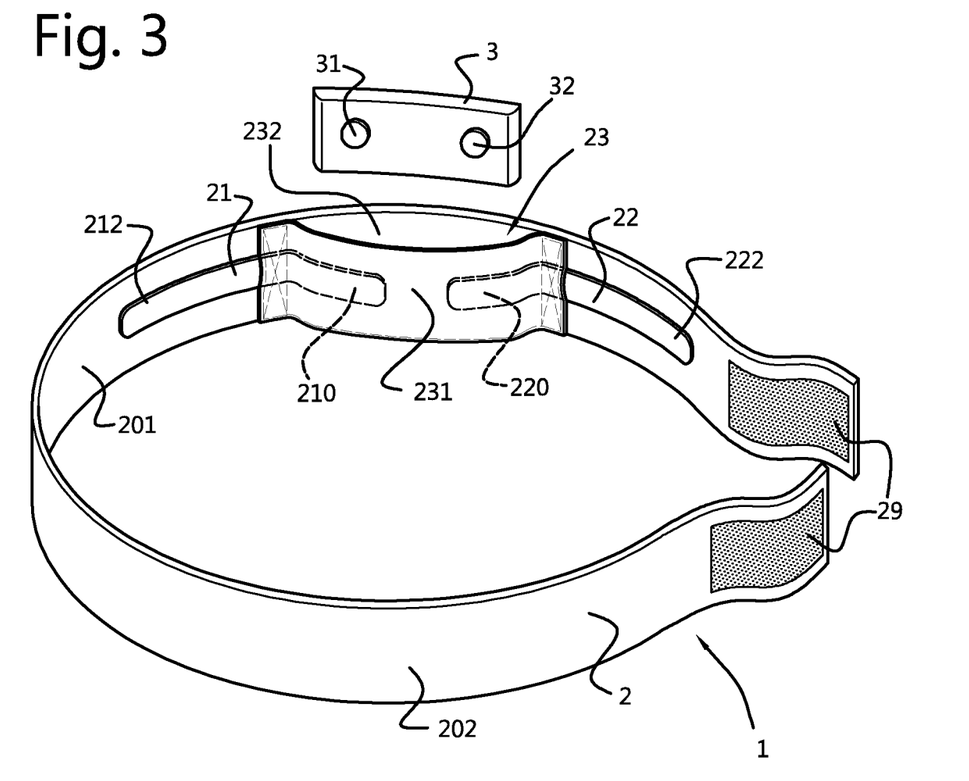
FIG. 3 shows a perspective exploded view of a sleep trainer according to the invention, wherein a first and second electrode are formed by a conductive fabric.
Figure 4:
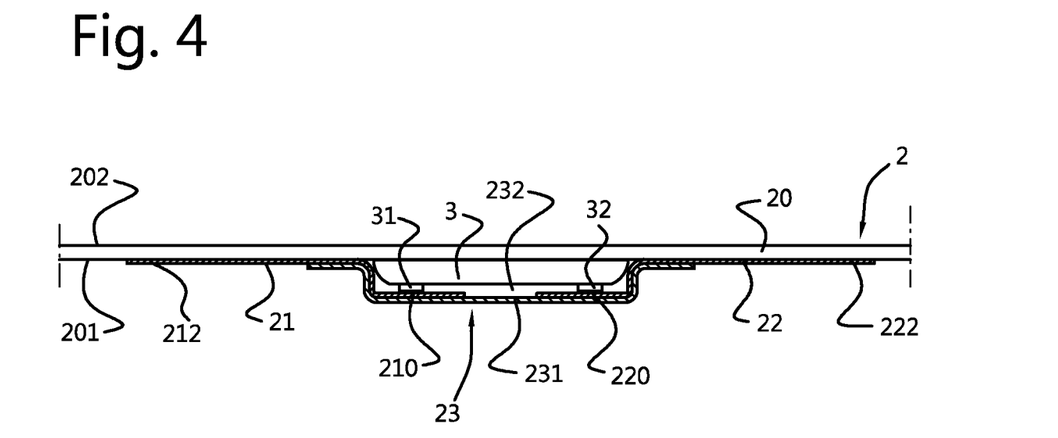
FIG. 4 shows a cross sectional view of the band as shown in FIG. 3, wherein monitor contact points are directed away from the body band.

The monitor has a first and second monitor contact point 31, 32. In FIGS. 1 and 2, the monitor contact points are positioned on the housing top surface 301. Preferably, as shown in FIGS. 3 and 4, the monitor contact points are positioned on the housing bottom surface 302. Each monitor contact point is flat. Each monitor contact point is coin shaped. Typically, each monitor contact point has a circular shape including an outer diameter of at most 10 mm, preferably at most 5 mm Each monitor contact point has a cylindrical body including flat end faces. Each monitor contact point 31, 32 hardly protrudes, in particular at most 1 mm, in particular at most 0.5 mm, preferably at most 0.3 mm above the housing top surface 301.

The monitor 3 is releasable connectable with the band 2. A person may manually connect or disconnect the monitor 3 with the band 2 by respectively inserting the monitor 3 into a band pocket 23 of the band 2 or removing the monitor 3 out of the band pocket 23.

The band pocket 23 has a band pocket opening 232 for receiving the monitor 3. The band pocket is formed by a band pocket wall 231. The band pocket wall may be made of a plastic material. Here, the band pocket wall comprises a stretchable pocket fabric. Here, the pocket fabric is oblong. The pocket fabric has a rectangular shape. The pocket fabric is manufactured by cutting off a fabric strip which is attached to the band body 20. Preferably, the pocket fabric is attached to the innerside of the band. Preferably, the pocket fabric is attached to the backside of the band body 20.

Preferably, the pocket opening 232 is provided at a frontside of the band. The pocket opening 232 may be a slotted opening. The opening may provide a passage through the band pocket 20. In an embodiment, the slotted pocket opening 232 may be provided with a pocket closure, like a zipper or overlapping flap, but preferably, the slotted opening 232 is free of additional features to prevent any obstacles which might reduce a wearing comfort.

The pocket opening 232 may be provided in an upper region of the pocket to allow a person to insert the monitor 3 into the band pocket 23 in a downwards movement.

In an embodiment, the pocket fabric forming the pocket wall 231 may be attached at three edges to the band body 20 leaving one edge free which free edge forms the band pocket opening 232. The geometry formed by the three attached edges of the pocket fabric corresponds with an outer contour of the monitor 3 which contributes to an accurate positioning of the of the monitor 3 with respect to the band 2.

The pocket fabric is elastic, such that a received monitor 3 gets clamped inside the band pocket. The pocket fabric 231 exerts a force onto the monitor 3 such that the monitor 3 is pressed onto the band body 20. The band contact points 210,220 are positioned inside the band pocket 23. By pressing the monitor onto the band body 20, the monitor contact points are pressed onto the band contact points.

FIG. 2 illustrates the band 2 of FIG. 1 in an enlarged sectional view. The electrodes 21, 22 are attached to the band body 20 at the band inner side 201. The electrodes 21, 22, the sensor pads 212, 222 and the band pocket 23 are provided at the band inner side 201 of the band body 20.

The first electrode 21 of the band 2 is positioned at a left side of the monitor 3. The second electrode 22 is positioned at a right side of the monitor 3. The monitor 3 is positioned in between the first and second electrode 21, 22. In wearing the sleep trainer 1, the person wears the monitor 3 at a central region of the chest which contributes to wearing comfort.

The electrodes 21, 22 extend along the band body 20. The electrodes 21, 22 include an electric wire to provide an electrical connection in between the sensor pads 212, 222 and the band contact points 210,220. The electric wire is connected to a sensor pad which is here a separate component. The electric wire is flexibly arranged to allow the band body to stretch which contributes to wearing comfort. The electric wire may be woven in a stretchable fabric attached to the band body 20. Preferably, both the band body 20 and the fabric holding the wire 21, 22 are stretchable which further contribute to the wearing comfort.

In FIG. 2, the monitor 3 is illustrated inside the band pocket 23. The pocket fabric 231 is stretched and presses the monitor contact points 31, 32 onto the band contact points 210, 220.

FIG. 3 shows a preferred embodiment of the sleep trainer 1. The sleep trainer 1 in this configuration provides a high level of wearing comfort. FIG. 4 illustrates the sleep trainer 1 of FIG. 3 in an enlarged sectional view. The electrodes 21, 22 extend along the band body 20. Each electrode 21, 22 is formed by a strip of conductive fabric which is attached to the band body 20. The conductive fabric may be attached by gluing, laminating or sewing. As is preferred, here the proximal ends of the electrodes 21, 22 are attached to the band pocket wall 231 at the band inner side 201. The strip of conductive fabric is stretchable, such that the proximal end of the conductive fabric can be sewn to the band pocket wall while keeping the band pocket wall 231 stretchable for pressing the contact points onto each other.

The strip of conductive fabric provides an electrical connection in between a distal and proximal end of the electrode. The distal end of each conductive fabric strip forms a sensor pad 212, 222. The proximal end of each conductive fabric forms a band contact point 210,220. The electrodes 21, 22 out of a conductive fabric contribute to a very flat-structure of the band.

Here, the sensor pads 212, 222 are incorporated in the conductive fabric. A free exposing surface section of the conductive fabric forms the sensor pad 212, 222. No separate items forming sensor pads are necessary. In wearing the band, the free exposing surface section of the conductive fabric contacts a body skin and a remaining section of the conductive fabric strip is covered. The proximal end of the conductive fabric strip is situated inside the band pocket and covered by the band pocket wall 231. The band pocket wall 231 partly covers the conductive fabric and herewith delimits the section forming the sensor pad.

The first electrode 21 formed by a first strip of conductive fabric extends at a first (left) side of the monitor 3. The second electrode 21 formed by a second strip of conductive fabric extends at an opposite (right) side of the monitor 3. The monitor 3 is positioned in a central region in between the first and second electrode. The monitor contact points 31, 32 mate with the band contact points 210,220. The band contact points 210,220 are spaced from each other at a distance of at least 5 mm, preferably at least 10 mm.

As further illustrated in FIG. 5, the monitor housing 30 houses a vibrator 33. The vibrator 33 is arranged to provide a tactile stimulus.

As further illustrated in FIG. 5, the monitor housing 30 houses a position sensor 34. The position sensor 34 is arranged to detect a position of a person wearing the sleep trainer 1. The position sensor 34 may for example be arranged to detect an upright position or a lying position of the person. Preferably, the position sensor 34 is arranged to detect a predetermined orientation in a lying position. The predetermined orientation is for example a supine, a prone, a left-sided, a right-sided or other position oriented with respect to a sagittal plane. A sleep trainer 1 including a position sensor 34 can be used as a sleep position trainer to alert a person wearing the sleep trainer in an event that the person is lying in a predetermined position. Preferably, such a sleep position trainer comprises a vibrator 33 to allow a tactile stimulus to stimulate a person to change position.

It is noted that the term "comprising" (and grammatical variations thereof) is used in this specification in the inclusive sense of "having" or "including", and not in the exclusive sense of "consisting only of".

Although the invention has been disclosed with reference to particular embodiments, from reading this description those of skilled in the art might appreciate a change or modification that may be possible from a technical point of view but which still do not depart from the scope of the invention as described above and claimed hereafter.

Modifications may be made to adapt a particular situation or material within the teaching of the invention and without departing from the essential scope thereof. It will be understood by those of skilled in the art that various changes may be made and equivalents may be substituted for elements thereof without departing from the scope of the invention. Therefore, the invention is not limited to the particular embodiments disclosed and illustrated in the above detailed description, but that the invention will include all embodiments falling within the scope of the appended claims.

Thus, the invention provides a sleep trainer comprising a band with two electrodes for carrying out an impedance measurement and a monitor for receiving a measurement signal. The band has a band pocket. An electrical connection is obtained by inserting the monitor into the band pocket. At least two band contact points are provided inside the band pocket. Monitor contact points are provided at an external surface of the monitor housing. The monitor contact points are flat and hardly protrude above the monitor housing. The band pocket prevents a lateral movement of the monitor and a band pocket wall exerts a pressing force to keep the monitor contact points in an abutting engagement with the band contact points. Advantageously, the sleep trainer provides a high level of wearing comfort which is required in a sleep disorder treatment to obtain treatment compliance.

REFERENCE SIGNS LIST 1 sleep trainer
2 band
20 band body
201 band innerside/backside
202 band outerside/frontside
21 first electrode
210 first electrode proximal end/first band contact point
211 first electrode distal end
212 first sensor pad
22 second electrode
220 second electrode proximal end/second band contact point
221 second electrode distal end
222 sensor pad
23 band pocket
231 band pocket wall, pocket fabric
232 band pocket opening
29 band closure
3 monitor
30 monitor housing
301 housing top surface
302 housing bottom surface
31 first monitor contact point
32 second monitor contact point
33 vibrator
34 position sensor

The invention claimed is:

1. A sleep trainer comprising:
a band including a band body including at least a first electrode and a second electrode for carrying out an impedance measurement; and
a monitor for receiving a measurement signal from the electrodes,
wherein the monitor is releasably connected to the band to allow a user to manually remove the monitor from the band,
wherein each electrode has an electrode distal end comprising a sensor pad exposed at an external surface at an inner side of the band in which the sensor pad is arranged for a skin contact,
wherein each electrode has an electrode proximal end exposed an externally accessible surface of the band forming a band contact point, and a band pocket for receiving the monitor,
wherein each band contact point is positioned inside the band pocket,
wherein the monitor includes a monitor housing for supporting electrical components,
wherein the monitor is provided with a first and second monitor contact point to obtain an electrical connection of the monitor with respectively the first and second band contact point of the first and second electrode,
where the monitor contact points are positioned at an external surface of the monitor,
wherein the band and the monitor contact points are arranged to obtain the electrical connection by an abutting engagement of the contact points, and
wherein the band pocket is dimensioned in correspondence with the monitor housing to mate the monitor contact points with the band contact points and wherein the band pocket has a band pocket wall which is stretchable to press the monitor contact points onto the band contact points.

2. The sleep trainer according to claim 1, wherein the first and second monitor contact points are flat.

3. The sleep trainer according to claim 2, wherein the monitor contact points protrude at most 1.0 mm, above an external surface of the monitor.

4. The sleep trainer according to claim 2, wherein the monitor contact points protrude at most 0.5 mm above an external surface of the monitor.

5. The sleep trainer according to claim 1, wherein the first and second monitor contact points are spaced at a distance, from each other.

6. The sleep trainer according to claim 1, wherein the first and second electrode are formed by an electrical conductive fabric, and wherein at least the sensor pad is formed by an exposed surface section of the conductive fabric.

7. The sleep trainer according to claim 1, wherein the band pocket is positioned at a backside of the band body at the band inner side.

8. The sleep trainer according to claim 1, wherein the band contact points are positioned on the band pocket wall.

9. The sleep trainer according to claim 1, wherein the sleep trainer is a sleep position trainer, which sleep position trainer is provided with a position sensor for detecting a body posture of a person wearing the sleep position trainer.

10. The sleep trainer according to claim 1, wherein the sleep trainer comprises a vibrator for generating a tactile stimulus.

11. The sleep trainer according to claim 1, wherein the band is a chest strap which is adapted for wrapping around a torso of a human's body.

12. The sleep trainer according to claim 11, wherein the monitor is positioned at the band, such that in use the monitor is positioned at a central position of the human's chest.

13. The sleep trainer according to claim 1, wherein the monitor housing is a moulded.

14. The sleep trainer according to claim 1, wherein the monitor housing is a layered item including a baseplate for supporting electronic components.

15. A band for a sleep trainer the band comprising:
a band body including at least a first electrode and a second electrode for carrying out an impedance measurement, wherein each electrode has an electrode distal end comprising a sensor pad exposed at an external surface at an inner side of the band in which the sensor pad is arranged for a skin contact, wherein each electrode has an electrode proximal end exposed at an externally accessible surface of the band to form a band contact point, and a band pocket for receiving a monitor is arranged for receiving a measurement signal from the first and second electrodes, wherein the band contact points are positioned inside the band pocket, and wherein the band pocket has a stretchable band pocket wall for pressing monitor contact points of a received monitor onto the band contact points.

16. The band according to claim 15, wherein the band contact points are positioned on the band pocket wall.

17. The band according to claim 15, wherein the band is incorporated into a garment.

18. The according to claim 17, wherein the garment is a tight fitting T-shirt, and wherein the band is located at a neck portion or chest portion of the garment.

19. A monitor for a sleep trainer including a thoracic impedance measurement band having a band body, the band body having a first electrode and a second electrode, wherein each electrode has an electrode proximal end which is exposed at an externally accessible surface of the band to form a band contact point, wherein the band has a band pocket for receiving the monitor, wherein each band contact point is positioned inside the band pocket, and wherein the band pocket has an elastic band pocket wall, the monitor comprising:

a monitor housing for housing electrical components, wherein the monitor housing is provided with a first and a second monitor contact point which are positioned at an external surface of the monitor housing and structured for electrically connecting the monitor to respectively the first and the second band contact point of the first and second electrode, and wherein the band and monitor contact points are arranged to obtain the electrical connection by an abutting engagement of the contact points, and wherein the monitor housing is sized and configured in correspondence with the band pocket to mate the monitor contact points with the band contact points.

20. The monitor according to claim 19, wherein the first and second monitor contact points are positioned at both sides of the monitor housing.

* * * * *